United States Patent
Roeher et al.

(10) Patent No.: US 6,423,022 B1
(45) Date of Patent: Jul. 23, 2002

(54) BLOOD PURIFICATION APPARATUS

(75) Inventors: Otfried Roeher, Dresden; Steffen Korth, Erfurt; Friedrich A. Mueller, Loehnberg; Dieter Rath, Melsungen, all of (DE)

(73) Assignee: B.Braun Melsungen AG, Melsungen (DE)

(*) Notice: Subject to any disclaimer, the term of this patent is extended or adjusted under 35 U.S.C. 154(b) by 0 days.

(21) Appl. No.: 09/310,994

(22) Filed: May 13, 1999

(30) Foreign Application Priority Data

May 14, 1998 (DE) .......................... 198 21 534

(51) Int. Cl.[7] ...................... A61M 37/00; A61M 31/00; B01D 61/00; C02C 1/00
(52) U.S. Cl. .................. 604/5.01; 604/67; 210/650; 210/646; 210/741; 706/924
(58) Field of Search .................. 604/65–67, 4–6, 604/4.01, 5.01–5.04, 6.09, 6.1, 6.11, 6.16, 28; 210/645–47, 650–51, 739, 741, 85, 87–90, 97, 98, 96.1–96.2, 134, 138, 143, 257.1–257.2, 258–59, 321.6, 805, 321.71–321.72, 321.75, 416.1, 929, 433.1, 434; 422/44, 48; 714/699, 819; 706/1, 3, 4, 8, 52, 55, 900, 924; 705/3

(56) References Cited

U.S. PATENT DOCUMENTS

| | | | | |
|---|---|---|---|---|
| 5,227,049 A | * | 7/1993 | Chevallet et al. ........... | 210/97 |
| 5,503,624 A | * | 4/1996 | Roeher et al. ............. | 604/65 |
| 5,620,608 A | * | 4/1997 | Rosa et al. | |
| 5,725,775 A | * | 3/1998 | Bene et al. ............... | 210/646 |
| 5,725,776 A | * | 3/1998 | Kenley et al. | |
| 5,865,174 A | * | 2/1999 | Kloeppel .............. | 128/204.23 |
| 5,910,252 A | * | 6/1999 | Truitt et al. ............. | 210/645 |
| 6,007,491 A | * | 12/1999 | Ling et al. .............. | 600/481 |

FOREIGN PATENT DOCUMENTS

| EP | 0 408 483 A1 | * 1/1991 | .......... A61M/5/172 |
|---|---|---|---|
| EP | 0652780 | 6/1994 | |
| EP | 0 967 554 A1 | * 1/1999 | ........... G06F/17/00 |

* cited by examiner

Primary Examiner—George R. Evanisko
Assistant Examiner—Patricia Bianco
(74) Attorney, Agent, or Firm—Diller, Ramik & Wight

(57) ABSTRACT

The ultrafiltration rate of a blood purification apparatus is controlled by a fuzzy control device in dependence on the patient's (16) blood pressure measured by a blood pressure monitor (24). For this purpose the blood pressure (P), a short-term blood pressure trend value (TRK) and a long-term blood pressure trend value (TRL) are fed as input variables for the fuzzy controller to the control device (23). The ultrafiltration rate (UFR) is determined by the volumetric ultrafiltration pump (36). According to the patient's (16) blood pressure situation a prestored profile of the ultrafiltration rate is modified. This avoids the necessity of an additional infusion to prevent too strong a blood pressure decrease.

13 Claims, 3 Drawing Sheets

BLOOD PURIFICATION APPARATUS

Figure 1:
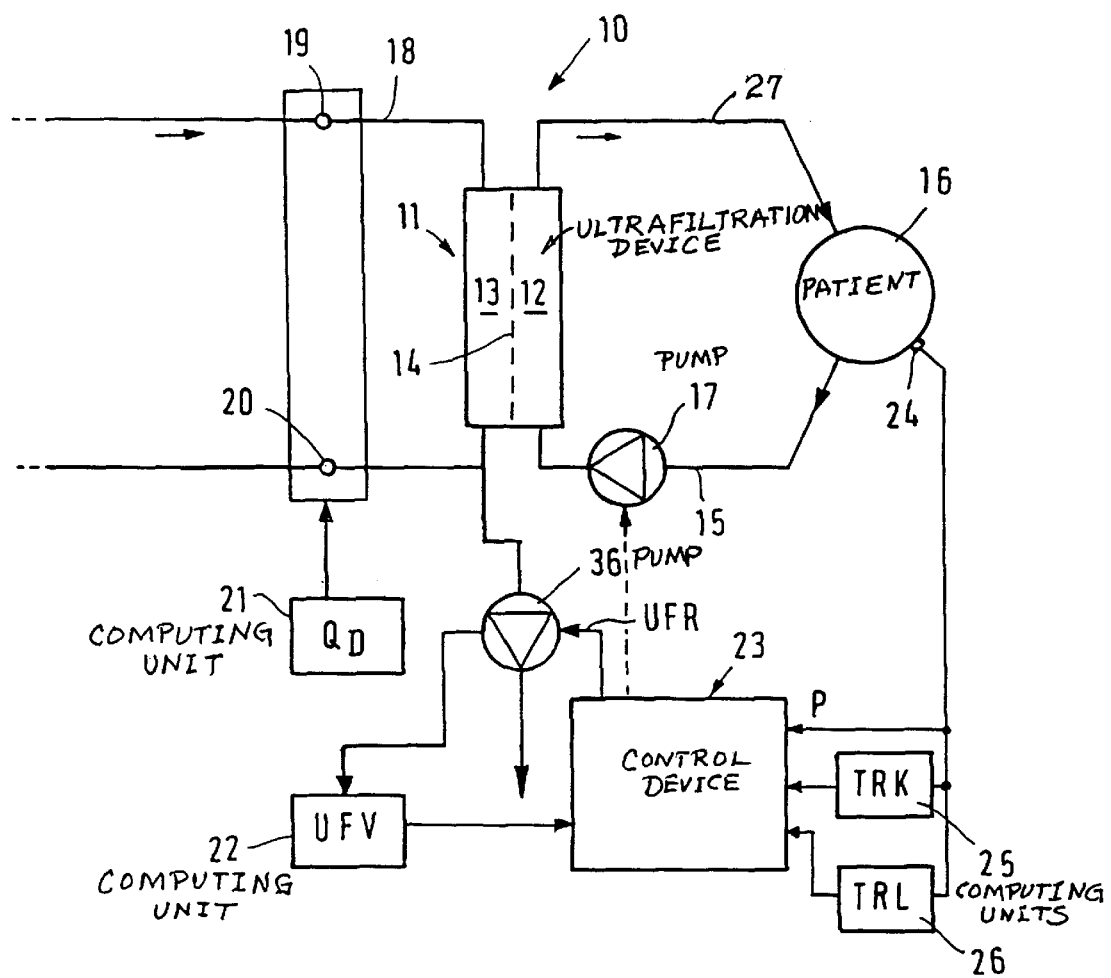

The invention relates to a blood purification apparatus comprising an ultrafiltration device, in which the ultrafiltration rate is controlled.

BACKGROUND OF THE INVENTION

During a blood purification treatment by means of haemodialysis, haemodiafiltration or haemofiltration the patient's blood is guided in an extracorporeal circuit through an ultrafiltration device and then returned into the patient's body. In the ultrafiltration device body fluid and contaminants are removed from the blood by means of convection and in the case of haemodialysis and haemodiafiltration additionally by means of diffusion in order to compensate for the renal insufficiency. In the following the processes of extracorporeal blood purification are referred to as "haemodialysis" in accordance with the medical usage. Due to partial or complete failure of the renal function the patient's body contains an excess of body fluid and contaminants dissolved therein at the onset of the treatment, which are removed via the blood circulation during the haemodialysis treatment. During the several hours of treatment there is the danger of serious blood pressure decreases (symptomatic hypotensions) as a result of the intensive removal of fluid. Such complications require immediate therapeutical measures for stabilisation of the blood pressure. It is common practice to infuse into the blood circulation a physiological saline solution (0.9% sodium chloride solution) as a substitute. This increases the blood volume and thus the blood pressure but simultaneously counteracts the necessary removal of fluid. The latter can be prevented by infusing smaller quantities of a highly concentrated (e.g. 20%) sodium chloride solution instead of larger quantities (e.g. 200–500 ml) of physiological saline solution. The considerably higher concentration of sodium ions in the solution as compared to that of the body tissue has the effect that by osmosis additional body fluid flows from the body tissue into the blood vessels. Infusion of a highly concentrated sodium chloride solution into the body requires however a more complex blood purification apparatus since an infusion pump necessitating a sophisticated control system must be provided.

U.S. Pat. No. 5,503,624 describes an infusion system with a controlling device in which the controlling device processes indistinct knowledge by means of linguistic variables and methods of the fuzzy logic. Several influencing components of different qualities are evaluated as indistinct knowledge and integrated in the automatic control of the infusion device taking into consideration their semantic meaning. This ensures control of the infusion of an additional fluid into the blood system during a dialysis treatment in such a way that the qualitatively different influencing components and the changes of their complex joint effects occurring during the treatment are recognised in accordance with their semantic meaning and included in the automatic infusion control.

European Patent EP 0 652 780 B1 describes a device for the prevention of hypotension in dialysis patients by replacing the infused hypertonic sodium chloride solution by an increased sodium concentration in the dialysis fluid (dialysate). For this purpose sodium is administered to the patient both via the dialysate as soon as a corresponding signal is generated by the patient or the medical personnel. However this is possible only when a blood pressure decrease entails symptoms which become aware to the patient. Sodium is dosed in accordance with predetermined values by means of a simple control system. Automatic control of the sodium dosage in dependence on the current blood pressure is not possible.

In the extracorporeal blood purification it is further common practice to adapt the ultrafiltration rate by so-called ultrafiltration profiles to the patient's condition. However it is only possible to adjust the respective value of the ultrafiltration rate for various phases of the blood purification treatment prior to the onset of the treatment. If necessary, the preselected ultrafiltration rates can be manually changed during the treatment by the medical personnel. The apparatuses used for this purpose are simple control devices with ultrafiltration rates arbitrarily set by the medical personnel. They do not possess any sensors for detecting changes in the patient's condition during the treatment.

Furthermore, it has been proposed to use sensors measuring the decrease in blood volume or the relative blood volume or the volume share of blood plasma or the volume share of the cellular blood constituents (haematocrit) to prevent the blood volume from excessively decreasing (hypovolaemia) during the haemodialysis treatment. The ultrafiltration rate is changed in dependence on the current measured values in such a way that the preselected default or limit values of these variables are met. These concepts are not suitable for an effective automatic blood pressure stabilisation since they do not directly measure the blood pressure behaviour and the aforementioned volume parameters take into consideration only part of the multi factorial causes which form the basis of the complex mechanisms of haemodialysis-induced hypotension.

It is therefore the objective of the present invention to provide a blood purification apparatus which automatically stabilises the patient's changing blood pressure by controlling the ultrafiltration rate.

SUMMARY OF THE INVENTION

According to the invention an ultrafiltration device controls the ultrafiltration rate in dependence on the blood pressure and at least one blood pressure trend value derived from the blood pressure by means of a fuzzy control. The ultrafiltration rate is the fluid volume removed from the patient's body per time unit via the membrane system of the ultrafiltration device. The ultrafiltration rate is not only preset by the control device but also automatically changed in dependence on the patient-related values. This showed that the blood pressure behaviour is a very informative parameter. During a dialysis treatment a blood pressure decrease (hypotension) may occur as a result of the removal of fluid from the blood system. The control device according to the invention can counteract such blood pressure changes in a suitable way by reducing the ultrafiltration rate in the case of excessive blood pressure decrease. Although an average value of the ultrafiltration rate is generally predetermined for the entire treatment, this value is changed by the blood pressure-dependent control when the blood pressure pattern indicates a situation requiring intervention. A special advantage offered by this device is that such an intervention is a change in the ultrafiltration rate so that an infusion of sodium chloride solution is not necessary. Thus the high costs of an infusion pump can be saved. However this does not preclude that in the case of an extreme course of the treatment drugs are for example manually injected. In certain cases it may be reasonable to include in the control not only the ultrafiltration rate but also the increase of the electrical conductivity of the dialysis fluid or infusion of a highly concentrated or isotonic infusion solution by means of a programmable infusion pump.

The concept of the invention allows for further physiological input variables to be used for fuzzy control, e.g. the change of the patient's blood volume as from the onset of the treatment (relative blood volume), or the change of the blood plasma volume (relative blood plasma volume), or the volume of the cellular blood constituents (haematocrit), the change of the ion concentration or of the electrical conductivity of the blood, the temperature of the blood or of the dialysis fluid.

The normal ultrafiltration profile used when the input variables of the fuzzy control do not meet abnormal values varies in accordance with an advantageous further development of the invention in dependence on the ultrafiltrate volume. The ultrafiltrate volume is the integral of the previous ultrafiltration rate and indicates the total fluid volume which has been removed from the body so far. Alternatively the ultrafiltration profile may depend on the time or any other physiological input variable, e.g. change of the ion concentration or the electrical conductivity of the blood. The ultrafiltration profile is in no case a preset rigid profile but is influenced by the measured blood pressure value and further input variables.

In accordance with a preferred further development of the invention the fuzzy controller receives the blood pressure value as well as a short-term and a long-term blood pressure trend value as input variables. Both trend values are integrated in the semantic domain blood pressure and allow judgement of the current blood pressure value including foresighted conclusions.

In the following an embodiment of the invention is explained in detail with reference to the drawings.

Figure 2:
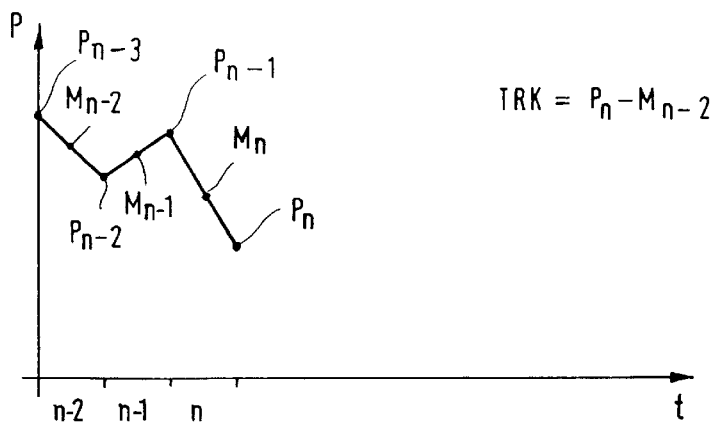
Figure 3:
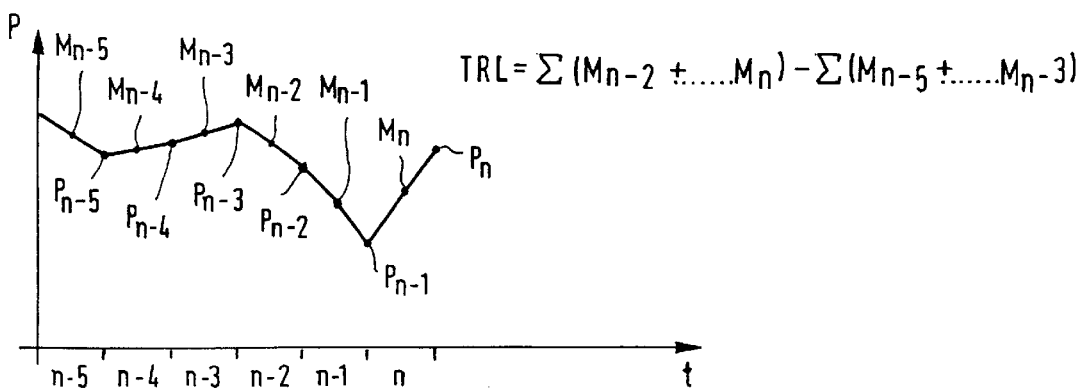
Figure 4:
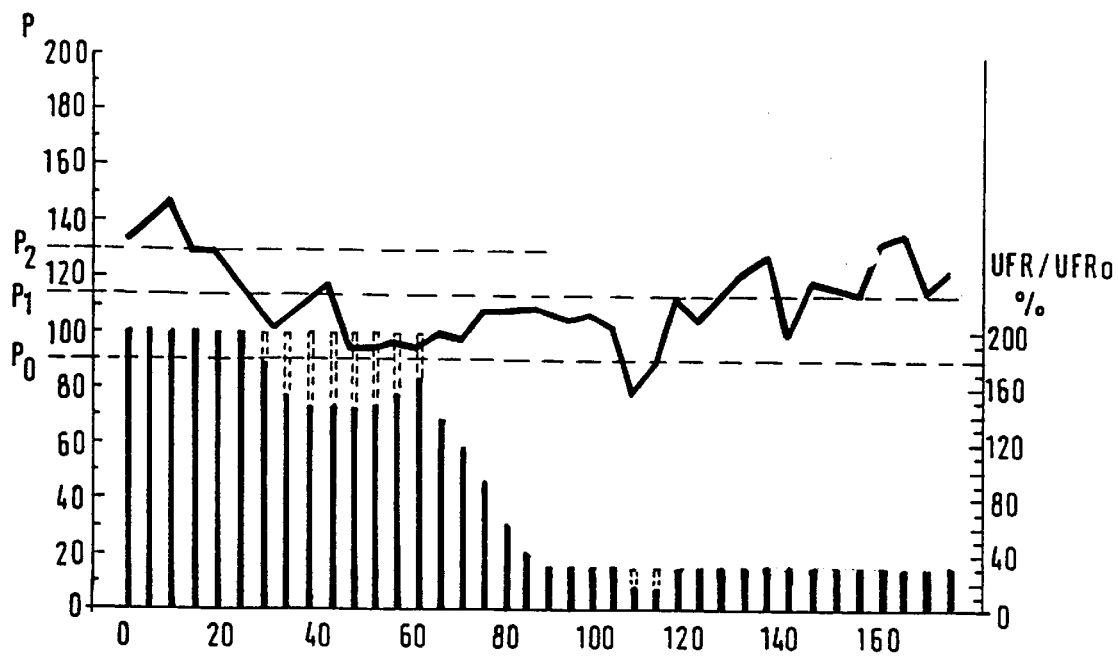
Figure 5:
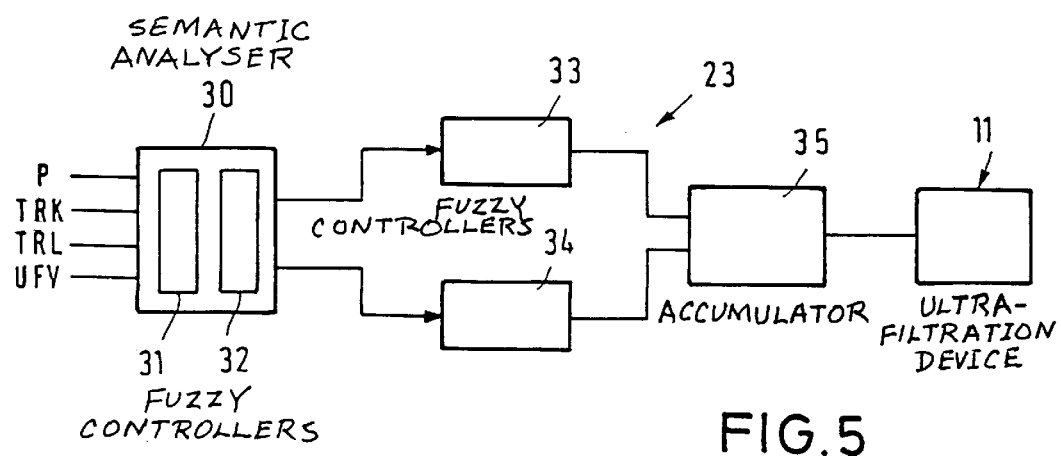

FIG. 1 shows a schematic diagram of the control principle of the blood purification apparatus, FIG. 2 shows a curve of the blood pressure pattern to explain the calculation of the short-term blood pressure trend value, FIG. 3 shows a curve of the blood pressure pattern to explain the calculation of the long-term blood pressure trend value, FIG. 4 shows a time diagram of blood pressure pattern and ultrafiltration rate, and FIG. 5 shows a diagram of the fuzzy control device.

DESCRIPTION OF THE PREFERRED EMBODIMENT

FIG. 1 shows a blood purification apparatus 10. The term blood purification apparatus is to be understood as a comprehensive term in such a sense that it covers an apparatus for haemodialysis as well as for haemofiltration or haemodiafiltration.

The blood purification apparatus 10 comprises an ultrafiltration device 11 with a primary chamber 12 and a second chamber 13 which are separated from each other by a membrane 14. The primary chamber 12 receives blood via a blood circulation path 15 taken from the arterial system of the patient 16 which is conducted to and purified in the ultrafiltration device 11 and is subsequently returned via a blood circulation path 27 to the patient's body 16 via the venous system. In the blood circulation path 15 a pump 17 is arranged which is executed as volumetric pump, i.e., the volume flow of this pump corresponds to the driving speed and is controllable.

The secondary chamber 13 of the ultrafiltration device 11 is arranged in a dialysis fluid path 18 where dialysis fluid is pumped. The dialysis fluid is taken from a storage container (not shown), takes up additional substances from the blood in the ultrafiltration device 11 and is then pumped to a discharge (not shown). In the dialysis fluid path flow chambers 19 and 20 are arranged upstream and downstream of the secondary chamber 13 which control the flow rate at the point concerned. The flow chamber 19 and the flow chamber 20 maintain the same flow rate. Via the volume-controlled ultrafiltration pump 36 the desired ultrafiltration flow is withdrawn. The dialysis fluid flow $Q_D$ is kept constant by a computing unit 21. The ultrafiltration rate UFR is fed to a computing unit. 22 which determines the time integral of the ultrafiltration rate and thus calculates the ultrafiltrate volume UFV, i.e. that fluid volume which has passed the membrane 14 since the onset of the treatment.

The ultrafiltration rate is controlled by means of the control device 23 which supplies control signals for the flow rate of pump 36. The flow rate of the pump is adjusted in such a way that the desired ultrafiltration rate is attained.

The control device 23 further receives the blood pressure signal P from a blood pressure monitor 24 which is attached to the patient's body 16. The blood pressure monitor comprises an inflatable cuff which is fastened around the patient's upper arm and carries out non-invasive blood pressure measurements at preset intervals of for example 5 minutes.

The blood pressure value P is fed to a computing unit 25 which calculates a short-term blood pressure trend value TRK and to another computing unit 26 which calculates a long-term blood pressure trend value TRL. Both trend values TRK and TRL are processed in the control device 23.

FIG. 2 shows the calculation of the short-term blood pressure trend value TRK. Along the abscissa the time t and along the ordinate the blood pressure P are plotted. Time t is subdivided into intervals n−2, n−1, n of 5 minutes. At the end of each interval the blood pressure is measured with the blood pressure values $P_{n-2}$, $P_{n-1}$ and $P_n$ being determined. The arithmetic mean value $M_{n-2}$ of the blood pressure in the interval n−2 is the mean value of the blood pressure values $P_{n-3}$ and $P_{n-2}$.

The short-term trend value TRK at the end of the interval n is calculated as follows:

$$TRK = P_n - M_{n-2}.$$

In the above example TRK is negative, i.e. the short-term trend value indicates a blood pressure decrease. If this blood pressure decrease exceeds a preadjusted limit value the control device intervenes.

FIG. 3 gives an example of the calculation of the long-term trend value TRL. Here, too, the blood pressure measurement intervals from n−5 to n are shown along the abscissa and the blood pressure P is plotted along the ordinate. To determine the long-term trend the mean values $M_{n-5} \ldots M_n$ are evaluated. These mean values of the individual intervals are determined by calculation from the measured blood pressure values defining these intervals.

The long-term trend TRL of the blood pressure is calculated as follows:

$$TRL = \Sigma(M_{n-2} + \ldots M_n) - \Sigma(M_{n-5} + \ldots M_{n-3})$$

Thus the sum of a certain number of mean values of coherent younger intervals is calculated and from this value the sum of the mean values of the coherent older intervals is subtracted. If value TRL is positive, this corresponds to an increasing trend of the blood pressure; if it is negative, this corresponds to a decreasing trend.

FIG. 5 shows the configuration of the control device 23. This control device carries out a fuzzy control. The details of such fuzzy control are described in the U.S. Pat. No. 5,503,624 which is incorporated in this description by reference. The control device 23 comprises a semantic analyser 30 to which the input variables P, TRK, TRL and UFV are fed. The semantic analyser has a first fuzzy controller 31 which aggregates the memberships, determined from the membership functions of the individual feature intervals for a total of 64 possible conditions by means of a set operator into overall memberships $c_{ges\ n}$ (n=1 . . . 64). A first semantic evaluation of the domain hypotension and ultrafiltration is carried out by calculation of the centre of gravity and moment of the overall memberships of all activated conditions of the domain.

For the further semantic evaluation stages the semantic analyser 30 possesses a domain evaluation unit 32 in which the medical knowledge regarding the medical importance of the various conditions and the conclusions are stored which are to be drawn taking into consideration the determined moments of the individual domains. In the second semantic evaluation stage each individual domain is weighted at a specified factor. On the basis of the result determined in the second semantic evaluation stage the domain evaluation stage 30 specifies the scope within which the fuzzy controllers of the second hierarchy level participate in the calculation of the ultrafiltration rates of the ultrafiltration device 11.

In the third semantic evaluation stage the domain evaluation unit 30 analyses whether there are overall memberships $c_{ges\ n}$ outside a predetermined field. This third semantic evaluation stage admits of both weighting factors analogous to the second evaluation stage as well as controversial weighting, e.g. if further physiological measuring variables are included as input variables in addition to the blood pressure pattern and if a strongly activated condition requires, from the medical point of view, an exclusively or primarily plasma volume-controlled ultrafiltration.

According to FIG. 5 the two fuzzy controllers 33, 34 are arranged in the second hierarchy level and these two controllers automatically multiply their domain-specific inference results by the respective value for the semantic overall evaluation of the domain concerned. The fuzzy controller 33 is assigned to the semantic domain hypotension and the fuzzy controller 34 to the semantic domain ultrafiltration. The control variable accumulator 35 aggregates the results of the individual domains and determines the overall control variable for the ultrafiltration device 11. For this purpose the sum of all semantic evaluations is set to 100 and the inference results of the individual fuzzy controllers 33, 34 are multiplied by the corresponding percentage share of their domains. The sum of the percentage shares of all domains normalised in this way directly indicates the ultrafiltration rate to be applied by the ultrafiltration device or by the corresponding adjustment of pumps 17, 36.

FIG. 4 shows the effect of the described control on the ultrafiltration rate. In the lower part of the diagram the relative ultrafiltration rate UFR/UFRo is shown with UFRo being the mean ultrafiltration rate. If for example a total of 4 ltrs. of fluid are to be removed by ultrafiltration within a period of 4 hours, the mean ultrafiltration rate UFRo is 1 ltr./hour. In the initial phase of the treatment a considerably higher ultrafiltration rate is applied in dependence on the blood pressure pattern, which amounts for example to twice the UFRo and is used to obtain a ultrafiltrate volume margin. Subsequent to the initial phase the ultrafiltration rate is automatically reduced to lower values which impose less strain on the patient's blood circulation. The high value applied in the initial phase is justified by the fact that in this phase the patient's body contains a large amount of excessive fluid so that a more intensive ultrafiltration is normally well tolerated. However in the course of treatment there is the danger that the risk of blood pressure decrease grows due to the ultrafiltrate volume withdrawn so far and the ultrafiltration rate increased as compared with UFRo.

The upper part of the diagram shows the overall blood pressure P pattern for a haemodialysis treatment, which is automatically measured as usual in mmHg at intervals of five minutes. The lower limit value $P_0$ defines the limit blood pressure to be individually preselected for each patient; if this limit blood pressure is fallen short of, it is absolutely necessary that the automatic control of the ultrafiltration rate is activated. In the blood pressure range between the limit values $P_0$ and $P_1$ the automatic control is activated only when signs of an imminent blood pressure decrease are detected by the control system in the result of a semantic analysis of the blood pressure pattern.

The presented curve of the blood pressure pattern shows that the ultrafiltration rate is changed in the indicated way both in dependence on the absolute blood pressure value P and in dependence on the trend values TRK and TRL. The ultrafiltration profile shown in FIG. 4 and completed by the dashed lines represents the profile prestored in the control device 23. The dashed lines which supplement the values of the normalised ultrafiltration rate in upward direction indicate the ultrafiltration rate in the event that the blood pressure is sufficiently high and does not show any tendency to strongly decrease, i.e. the preprogrammed pattern of the ultrafiltration rate at a stable blood pressure pattern.

This profile is modified by the actual course of the blood pressure in the indicated way. In the situation shown it is necessary to reduce the ultrafiltration rate at several intervals so that at a definite point of time the ultrafiltrate volume is lower than that ultrafiltrate volume which could have been withdrawn at a stable blood pressure pattern according to the stored profile. Since in this example the stored ultrafiltration profile depends on the ultrafiltrate volume, transition to lower ultrafiltration rates is effected only when a definite percentage of the total ultrafiltrate volume to be withdrawn has been reached, e.g. 70%.

Another possibility would be not to programme the ultrafiltration profile for a stable blood pressure pattern prestored in the control device 23 in dependence on the ultrafiltrate volume but in dependence on the duration of treatment. Further alternatives provide for specifying the ultrafiltration profile for a stable blood pressure pattern in dependence on other input variables. Such input variables are in particular the relative blood volume, the relative blood plasma volume and the volume of the cellular blood constituents (haematocrit), the ion concentration and the electrical conductivity of the blood or the temperature of the blood or of the dialysis fluid. In all alternatives the prestored ultrafiltration profiles for a stable blood pressure pattern are modified by the actual course of the blood pressure pattern in the described way.

What is claimed is:

1. A blood purification apparatus comprising ultrafiltration means (11) for purifying blood, first means (15) for conducting blood from a patient to said ultrafiltration means (11), second means (27) for conducting blood from said ultrafiltration means (11) to the patient, means (23) for controlling the rate of blood flow through said first and second blood conducting means (15, 27), means (24) directly located at the patient's body for measuring patient blood pressure (P), means (25 or 26) for determining at least one blood pressure trend value (TRK or TRL), and said controlling means (23) including fuzzy controller means (31) responsive to said measured blood pressure (P) and said at least one blood pressure trend value (TRK or TRL) for automatically affecting patient blood pressure stabilization.

2. The blood purification apparatus as defined in claim 1 including means (17) in fluid communication with said first blood conducting means (15) and responsive to the output of said fuzzy controller means (31) for affecting patient blood pressure stabilization.

3. The blood purification apparatus as defined in claim 2 including means (22) for generating an ultrafiltration volume (UFV) of said ultrafiltration means (11); and said controlling means (23) includes analyzing means (30) responsive to said measured blood pressure (P), said at least one blood pressure trend value (TRK or TRL), and the generated ultrafiltration volume (UFV) for generating an ultrafiltration profile dependent upon variable ultrafiltration volume (UFV).

4. The blood purification apparatus as defined in claim 2 including means (22) for generating an ultrafiltration volume (UFV) of said ultrafiltration means (11); and said controlling means (23) includes analyzing means (30) responsive to said measured blood pressure (P), said at least one blood pressure trend value (TRK or TRL), and the generated ultrafiltration volume (UFV) for generating a time dependent ultrafiltration profile dependent upon variable ultra filtration volume (UFV).

5. The blood purification apparatus as defined in claim 2 wherein said controlling means (23) includes analyzing means (30) responsive to said measured blood pressure (P) and said at least one blood pressure trend value (TRK or TRL) for generating an ultrafiltration profile dependent upon a physiological input variable.

6. The blood purification apparatus as defined in claim 1 including pump means (17) in fluid communication with said first blood conducting means (15) and responsive to the output of said fuzzy controller means (31) for affecting patient blood pressure stabilization by controlling the blood flow rate through said first blood conducting means (15).

7. The blood purification apparatus as defined in claim 1 including means (22) for generating an ultrafiltration volume (UFV) of said ultrafiltration means (11); and said controlling means (23) includes analyzing means (30) responsive to said measured blood pressure (P), said at least one blood pressure trend value (TRK or TRL), and the generated ultrafiltration volume (UFV) for generating an ultrafiltration profile dependent upon variable ultrafiltration volume (UFV).

8. The blood purification apparatus as defined in claim 7 wherein said fuzzy controller means (31) combines inputs (P, TRK, TRL, UFV) thereto to form semantic domains arranged in one condition scale for each domain and determining for each condition of a condition scale a membership value (Cges).

9. The blood purification apparatus as defined in claim 8 including evaluation means (32) for carrying out a domain-specific weighing of said membership values (Cges) and performing a semantic evaluation for each domain.

10. The blood puriiciation apparatus as defined in claim 9 including second and third fuzzy controllers (33, 34) for forming a domain-specific control variable from the membership values (Cges) of the domain and semantic evaluation.

11. The blood purification apparatus as defined in claim 10 including accumulator means (35) for aggregating the domain-specific control variables of several domains into one control variable for controlling the operation of said ultrafiltration means (11).

12. The blood purification apparatus as defined in claim 1 including means (22) for generating an ultrafiltration volume (UFV) of said ultrafiltration means (11); and said controlling means (23) includes analyzing means (30) responsive to said measured blood pressure (P), said at least one blood pressure trend value (TRK or TRL), and the generated ultrafiltration volume (UFV) for generating a time dependent ultrafiltration profile dependent upon variable ultrafiltration volume (UFV).

13. The blood purification apparatus as defined in claim 1 wherein said controlling means (23) includes analyzing means (30) responsive to said measured blood pressure (P) and said at least one blood pressure trend value (TRK or TRL) for generating an ultrafiltration profile dependent upon a physiological input variable.

* * * * *